United States Patent [19]

Lemelson

[11] Patent Number: 4,764,359
[45] Date of Patent: * Aug. 16, 1988

[54] DRUG COMPOSITIONS AND THEIR USE IN TREATING HUMAN OR OTHER MAMMALIAN PATIENTS

[76] Inventor: Jerome H. Lemelson, 48 Parkside Dr., Princeton, N.J. 08540

[*] Notice: The portion of the term of this patent subsequent to May 19, 2004 has been disclaimed.

[21] Appl. No.: 809,207

[22] Filed: Dec. 16, 1985

Related U.S. Application Data

[63] Continuation-in-part of Ser. No. 631,605, Jul. 17, 1984, Pat. No. 4,674,480, and Ser. No. 614,038, May 25, 1984, Pat. No. 4,665,897, and Ser. No. 614,021, May 25, 1984, Pat. No. 4,671,256.

[51] Int. Cl.[4] .................... A61K 49/00; A61K 39/00; A61K 9/22
[52] U.S. Cl. ........................ 424/1.1; 424/85; 424/450; 424/457; 424/9
[58] Field of Search ........................ 424/1.1, 9, 19, 85, 424/450, 457

[56] References Cited

U.S. PATENT DOCUMENTS

| | | | |
|---|---|---|---|
| 3,474,777 | 10/1969 | Figge et al. | 128/1.3 |
| 4,323,056 | 4/1982 | Borrelli et al. | 128/1.3 |
| 4,448,765 | 5/1984 | Ash et al. | 424/1.1 |
| 4,452,774 | 6/1984 | Jones et al. | 424/1.1 |
| 4,541,438 | 9/1985 | Parker et al. | 128/664 |
| 4,558,690 | 12/1985 | Joyce | 604/20 |
| 4,590,922 | 5/1986 | Gordon | 128/1.3 |

*Primary Examiner*—Christine M. Nucker

[57] ABSTRACT

Drug compositions formed as individual units, a multitude of which are employed as one or more doses, to reduce or aleviate cancer in a living being by targeting to and destroying cancer cells. In a preferred form, each drug unit is formed of an antibody, such as a monoclonal antibody targeted to a specific type of antigen, such as defined by a specific form of cancer, which antibody is united with or bonded to a white blood cell such as a macrophage or lymphocyte, preferably one which has been treated or activated with an immune system activator of a class referred to as lymphokines. One of such activators which may be so employed, is interleukin-2, which, in one embodiment, forms part of the drug unit. The drug unit may also include a microcapsule containing one or more of such lymphokine activated killer cells encapsulated therein and releasable therefrom, preferably after the drug unit has been targeted to a cancer cell or tumor by the antibody attached thereto. In a particular form, both the antibody and one or more of the white blood cells, lymphocytes or macrophages, cooperate in attacking the cancer cell or cells at the targeted site and the procedure progresses as cancer cells are destroyed exposing other cancer cells to additional drug units which feed to the cancer site in blood flow, in a manner to totally destroy the tumor or put into regression.

20 Claims, 2 Drawing Sheets

DRUG COMPOSITIONS AND THEIR USE IN TREATING HUMAN OR OTHER MAMMALIAN PATIENTS

RELATED APPLICATIONS

This is a continuation-in-part of copending application Ser. No. 631,605 filed July 17, 1984, now U.S. Pat. No. 4,674,480 and application Ser. No. 614,038 filed May 25, 1984, now U.S. Pat. No. 4,665,897 and Ser. No. 614,021 filed May 25, 1984, now U.S. Pat. No. 4,671,256.

BACKGROUND OF THE INVENTION

1. Field of the Invention

This invention is in the field of compositions of matter such as drug units, applied in the form of doses thereof to treat or cure a disease, such as cancer. Drug units are formed of cancer cell killing biological elements, such as white blood cells, which are targeted to specific cancer cells by antibodies or antibody fragments bonded to such white blood cells, coating material thereon or a microcapsule or vesicule in which one or more of such cells are encapsulated.

2. The Prior Art

It is known to produce antibodies by genetic engineering, referred to as monoclonal antibodies, which are surface configured and constructed to permit them to target to or be retained against specific antigens in a living being, such as specific types of cancer cells. Marker-specific antibodies have been produced by a number of techniques such as disclosed in the text "Immunodiagnosis of Cancer", Herberman et al, Eds. (Marcel Dekker, Inc., New York and Basel, 1979) and in the text "Cancer Markers", Sell, Ed. (Humana Press, Clifton, N.J. 1980). U.S. Pat. Nos. 3,927,193; 4,036,945; 4,331,647; 4,444,744; 4,460,959; 4,460,561; 4,172,124 and others describe methods for producing monoclonal antibodies and antibody fragments which are specific to cancer cells or tumor associated markers to permit them to be used for cnacer detection, localization and therapy. Other U.S. Patents which teach the production of monoclonal antibodies include: U.S. Pat. Nos. 4,434,230; 4,423,034; 4,381,925; 4,364,397 and 4,364,396.

It is also known in the art to secure or bind such monoclonal antibodies or incorporate therein radioactive materials and particles of radioactive or inactive nuclides for the purposes of detecting and treating cancer when the antibodies target to specific cancer cells, such as existing on the surface of tumors. U.S. Patents to Goldbenberg, Nos. 4,331,647; 4,444,744; 4,460,559; 4,460,561; & 4,348,376 & 4,311,688 disclose disclose tumor localization and therapy using labled antibody fragments and include methods for producing such labled fragments or drug units.

A method for entrapping therapeutic agents within cells is disclosed in U.S. Pat. No. 4,446,951 to Pittman.

Various methods are also known in the art for effecting the production of microcapsules such as liposomes and the like. Unilamellar vesicles are described in U.S. Pat. No. 4,310,506 while various types of liposomes including certain which are polymer stabilized and their production are described in U.S. Pat. Nos. 4,448,765; 4,310, 505; 4,310,506 and 4,429,008 and the references therefore. Cancer drug delivery techniques and compositions are disclosed in U.S. Pat. Nos. 4,460,560 and 4,446,951 and the references therefore.

The treatment of cancer in living beings has involved a variety of techniques, each of which suffers shortcomings and serious side effects. Therapy employing radioactive materials, such as radioisotopes injected into the tissue or bloodstream of a living being or radiation directed through the body to a cancer site, detrimentally affects or destroys normal as well as diseased tissue or cancer cells. Chemical agents injected into the body also results in destroying or detrimentally affecting healthy tissue.

Recently, doses of lymphocytes produces from a patient's own blood and activated with an immune system activator, such as interlukin-2, a natural substance derived from the body and producable by genetic engineering, have been administered to persons with cancer by injection and allowed to circulate in the blood with positive results in the form of tumor remission. However, such technique suffers shortcomings associated with any drug which is administered in large doses to circulate freely in the bloodstream until a portion thereof encounters a tumor which may be localized at one site in the body remote from the point of injection of the drug. Side effects may also include atack by such killer lymphocyte cells on healthy tissue cells and/or other beneficial factors in thebody. Such technique also involves the use of relatively large doses of such activated lymphocytes as only a portion of those administered reach and react on the disease or cancer site.

SUMMARY OF THE INVENTION

This invention relates to improvements in drug compositions which are particularly useful in treating tumors and malignancies in living beings, as well as methods for making and applying such drug compositions to living beings with cancer. Such drug compositions are composed of multitudes of drug units which are formed of antibodies or antibody fragments and white blood cells such as specially treated and activated lymphocytes, which become killer cells for attacking specific types of cells such as cancer cells existing within a living being. By forming and administering select amounts of such drug units in one or more doses thereof to a person having a tumor or malignancy, the antibody portions of the drug units serve to target or attach the drug units to tumor or cancer cells of the malignancy whereafter the cell destroying killer cells of the drug units, which are so targeted adjacent the cancer, each attack individual cancer cells of the malignancy or tumor and destroy or weaken same a degree such that a subsequently applied lymphocyte or killer cell may destroy the cancer cell. In a particular form, one or more antibodies and/or antibody fragments form part of each drug unit which consists of a microcapsule or vesicule containing one or a plurality of killer cells such as activated lymphocytes, macrophages, lukacytes or the like, to which microcapsule is attached such antibody or antibody fragment(s) to permit the drug unit to be targeted thereby to a specific type of cancer cell, known to exist within the living being to whom the drug units are administered. After being so targeted, the microcapsule or vesicule is operable to dissolve or biodegrade under the action of body fluid or externally applied radiation or to otherwise open and release its contents immediately adjacent or against the diseased or cancerous tissue to which it is targeted, permitting the killer cell or cells thereof to attack and destroy the cells of such tissue. If the dose of such drug units or a plurality of select doses thereof are properly timed and administered, the procedure of destroying the tumor or malignancy may be controlled in its progression and optimized. In a preferred form, a computer or computers may be employed to analyze signals generated by sensing means, such as a detector or detectors of body fluid or blood components, radiation passing through the tumor site or emitted therefrom and other variables indicative of the type and extent of the cancer, and to control the treatment thereof by controlling both the preparation and administering of such drug units to a patient so as to predetermine and optimize the results of treatment.

Accordingly it is a primary object of this invention to provide new and improved drugs and drug units for use in treating diseases such as cancer and other diseases by the targeted destruction of disease cells, such as cancer cells, and methods for attaining such treatment with such drugs.

Another object is to provide an improved method for localizing the treament of a tumor or malignancy with so called killer cells, such as activated lymphocytes and the like.

Another object is to provide a system and method for administering disease killing agents, such as lymphokine activated lymphocytes to a living being with a malignancy or a plurality of malignancies, in a manner whereby most of the killer cells target to respective cancer cells within a short time after entering the body.

Another object is to provide a system and method for administering cancer killing cells to a living being with cancer, in a manner to permit such cancer killing cells to attack only the cells of the cancer.

Another object is to provide drug units which include one or more cancer destroying phages or lymphocytes which are targeted to and released at the site or sites of cancer, thereby optimizing the use of such drug unis and lessening side effects which may be due to the release or flow of such units to locations in the body which do not contain cancer cells.

Another object is to provide drug units composed of an antibody or antibody fragment targeted to a specific type of cancer cell bound to a macrophage or lymphocyte which has been treated, such as by means of a coating thereon, to permit the two to coexist without attacking each other, whereby such drug units are so constructed to permit the lymphocyte or macrophage to be released at the site of a cancer and to immediately attack a cell of the cancer.

Another object is to provide a drug unit composed of a microcapsule containing a plurality of cancer killing cells which are controllably released therefrom at a cancer site to permit such killer cells to cooperate in penetrating and destroying cancel cells adjacent the drug unit.

Another object is to provide improved drugs formed of drug units composed of one or more antibodyes and/or antibody fragments targeted to specific disease or cancer cells, wherein a multitude of such drug units are mixed in a fluid with antibodies and/or activated lymphocytes per se which are targeted to specific types of disease cells existing in the blood and/or lymth fluid to attack and kill same simultaneously as the contents of the drug units are targeted to and react on diseased tissue cells, such as cancer cells of a tumor.

Another object is to provide a drug unit composed of one or more antibodies and one or more macrophages or activated killer lymphocytes, wherein the antibody is targeted to a specific cancer cell and together with the killer cell attached thereto, cooperate in attacking and killing or weakening the same or adjacent cancer cells at the site to which the antibody targets.

Another object is to provide drug units in the form of capsules containing one or more whiLe blood cells, such as cancer killing lymphocytes in a liquid therein which liquid comprises or contains an immune system activator, such as interluken-2 for timulating and/or growing lymphocytes within such capsules.

Another object is to provide drug units in which lymphocytes are grown and/or stimulated to become killer cells, which drug units may be administered to a living being or stored in a body implant or the like and controllably released therefrom to permit them to attack and destroy cancer cells in the blood or adjacent tissue.

Another object is to provide a method for controllaby releasing cancer killing elements, such as killer cells, into the bloodstream of a living being to provide same for attacking and killing cancer cells which may exist in the blood.

Another object is to provide a system and method for controllably releasing an immune system activator, such as interluken-2 into the bloodstream to stimulate and effect the growth of disease fighting macrophages or lymphocytes.

Another object is to provide improved drug units formed of microcapsules containing a plurality of disease or cancer killing cells and means for timing the release of same in a manner to effect the incremental destruction of a tumor by such killer cells.

Another object is to provide a system and method for targeting a multitude of killer cells to a tumor in a living beams and releasing or utilizing same at the site of the tumor in a manner to permit the tumor to be partly or completely destroyed by exposing fresh tumor cells existing within the tumor by the destruction of outer layers of tumor cells with killer cells to permit subsequently applied killer cells to destroy the exposed cells.

Another object is to provide drug units for use in detecting and treating cancer, which units include an antibody or antibody fragment or a plurality of same attached to a composite material including one or more macrophages or activated lynphocytes and a tracer element, such as a radioactive isotope or inactive nuclide activatable with external radition for marking and detecting the tumor site to which the antibody targets.

With the above and such other objects in view as may hereinafter more fully appear, the invention consists of the novel combinations and arrangements of biological and chemical elements, where employed, making up the drug units, and the methods for applying and utilizing same described herein, but it is to be understood that changes, variations and modifications may be resorted to which fall within the scope of the invention as claimed.

BRIEF DESCRIPTION OF THE DRAWINGS

FIG. 10 is a side view of a drug unit formed of an antibody and a microcapsules, shown in cross secion, containing a plurality of killer white blood cells or macrophages.

Figure 1:
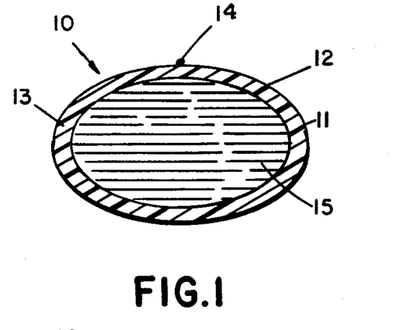
FIG. 1 is a cross sectional side view of a drug unit defined by a bulbous capsule containing one or more chemicals and one or more particles of a nuclide.

In FIG. 1 is shown a first form of the invention defined by a drug unit 10, which may comprise one of a multitude of such units disposed in a liquid or capsule which is administered to a living being. The drug unit 10 comprises a bulbous capsule 11, shown as having a spherical or ellipsoidal shape, although it may have any other suitable shape, with a side wall 12 completely surrounding contents 15 which may comprise any suitable type of medication such as an organic or inorganic liquid chemical, a plurality of such chemicals, a biological material, such as an antibiotic or a liquid containing one or more living or killed virus, bacteria, antibodies, phages, or other material which is desired to be dispensed within or in the immediate vicinity of disease tissue or disease cells existing within a living being.

Figure 2:
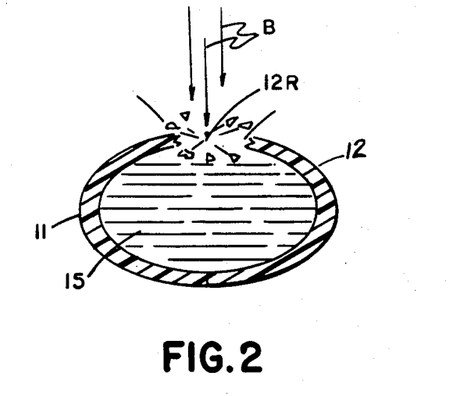
FIG. 2 is a side view in cross section of the drug unit of FIG. 1 having a portion of its sidewall destroyed or ruptured when a particle or particles of a nuclide attached to its sidewall, is rendered radioactive and explodes against the sidewall.

Shown supported against a portion of the outside surface 13 of the wall 12 of capsule 11 is a small particle 14 of a nuclide material, such as boron-10 or one of the nuclides described in my hereinabove setforth patent applications. Such nuclide 14 may comprise a plurality of particles bonded by means of a suitable resin or other material coating the outside surface 12A of all 12 of capsule 11, which particle or particles may be rendered radioactive and caused to generate radiation or explode as illustrated in FIG. 2, in a manner to rupture a portion of the wall 12 to permit the contents 15 of the capsule to flow through the opening 12R. A plurality of openings may be formed in the wall when particles of such nuclide are simultaneously rendered radioactive. Such particle or particles may be so rendered radioactive when the drug unit 10 is disposed or flows to a select location within a living being, such as a location of diseased tissue, dead or calcified tissue or bone desired to be subjected to a chemical or biological agent, such as the contents 15 of the capsule 11.

The contents 15 of the capsule 11 may be under slight pressure during the formation of the capsule or may be pressurized as the result of the heat or pressure of the radiation generated when the particle or particles 14 become radioactive. Accordingly, one or more of such particles may also be disposed within the body of the contents 15 or against the inside surface of the wall 12 or within such wall for such purpose and/or to render the wall 12 ruptured or porous to permit flow of the contents 15 from the capsule and/or absorption of body fluid into the capsule to mix or react with its contents.

The capsule 11 may vary in size from less than a thousandth of an inch in diameter to several thousandths of an inch in diameter or more, if a multitude of such capsules are utilized to deliver a chemical or biological agent to a particular location within a living being via the bloodstream or by direct injection to such location. It may also comprise a larger capsule which is injested by mouth, inserted by catheter or implanted by means of surgery at a select location in tissue or a body duct.

The wall 11 may be made of a synthetic polymer, such as a suitable plastic resin, a starch, protein, fat, cell tissue, combination of such materials or other organic matter. It may be employed per se or in combination with other elements as described hereafter. Similar or differently shaped capsules of the types illustrated in the drawings may be combined or mixed and may contain a plurality of different elements or drugs mixed in each or provided in separate capsules for cooperating in alleviating a malady such as by attacking or destroying bacteria or diseased tissue, improving the condition of living cells, changing the structure of living tissue or cells, dissolving or destroying tissue cells, repairing cells or cell damage, etc.

Figure 3:
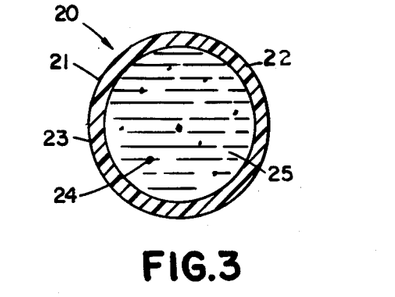
FIG. 3 is a side view in cross section of a spherically shaped drug unit and its contents.

In FIG. 3, a drug unit 20 of the type shown in FIGS. 1 and 2, comprises a spherically shaped container or capsule 21 of one or more of the materials described, with a spherical sidewall 22, the outer surface 23 of which may contain one or more particles of a nuclide of the type described and/or one or more antibodies, such as monoclonal antibodies, attached thereto by means of a suitable resin or assembled with the container 21 by means of a suitable derivatizing agent. Disposed within the hollow interior of spherically shaped container 21 is a liquid material or drug 25 having one or more particles 24 of a nuclide or a plurality of nuclides floating or supported therein. Such nuclide or nuclide particles 24 may be rendered radioactive, as in FIG. 2, by directing a beam or beams of radiation such as neutrons at the drug unit 20, preferably from a source thereof located exterior of the body in which the drug units are disposed, which neutrons render the one or more particles 24 radioactive in a manner to either explode or generate sufficient radiant energy to cause the liquid contents 25 to at least partially evaporate or otherwise expand in a manner to force such contents through the wall 21, which may be porous or rendered porous or may be ruptured by the internal pressure effected when the particle or particles 24 become radioactive. In such a manner, the contents 25 may be completely or partially expelled from the container and applied to adjacent or ambient tissue or disease matter located within a human living being adjacent the drug unit 20. In a particular form of FIG. 3, one or more particles of a nuclide disposed on the outer surface 23 of the wall 21 may be rendered radioactive and explode to rupture a portion or portions of the wall, rendering same porous or providing an opening therein or destroying such wall so that the contents 25 may flow therefrom to surrounding material.

In a modified form of the embodiments of FIGS. 1 and 3, the contents 25 of the microcapsules may comprise a plurality of other microcapsules containing chemical and/or biological elements to be released therefrom, certain at a different time or times than others, as the material(s) of the microcapsules biodegrade at one or more of a plurality of different release rates upon contact with body fluid.

Figure 4:
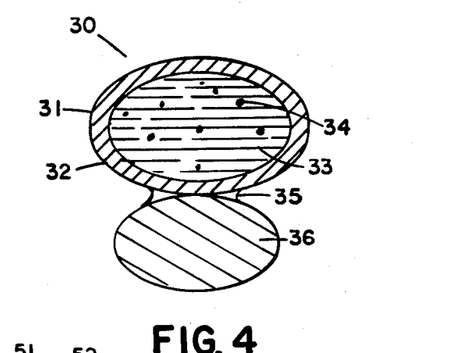
FIG. 4 is a side view in cross section of a drug unit which comprises a capsule containing a chemical or biological agent and one or more particles of a nuclide and an antibody, such as a monoclonal antibody, attached to a portion of the side wall of the capsule.

In FIG. 4 is shown a modified form of drug unit 30 formed of a capsule 31 of the type illustrated in FIGS. 1 and 2 or 3, with an spherical or ellipsoidally shaped sidewall 32 completely surrounding a liquid, cream or solid drug or chemical 33 having one or more particles 34 of a nuclide or nuclides disposed therein for use as described above. Bonded or otherwise attached to a portion of the exterior surface 32 of wall 31 is an antibody 36, such as a monoclonal antibody, which is targeted to a specific antigen located within a living being. Such antigen may comprise, for example, the surface of a cancer cell, bacteria, disease tissue or other material desired to be affected by the chemical or agent 33 released from the capsule 31 when the nuclide particle, particles 34 or same located within the contents 33 or disposed within or against the surface of the wall 32 of the capsule, are rendered radioactive and explode or generate sufficient heat or radiation to effect one or more of the described actions with respect to the wall of the capsule, such as render same porous or ruptured. Notation 35 refers to a polymer or other derivatizing agent employed to bond the antibody or monoclonal antibody 36 to a portion of the surface of the capsule 31.

Figure 5:
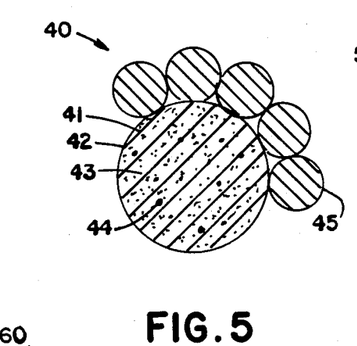
FIG. 5 is a side view in cross section of a drug unit formed of a spherically shaped central body having a plurality of antibodies attached to its exterior surface.

In FIG. 5 is shown a modified form of FIG. 4 wherein a drug unit 40 is composed of a base unit or container 41 which is illustrated as a porous spherical body, the cells 43 of which contain a drug or chemical dispensed therefrom to surrounding fluid or tissue. One or more particles 44 of a nuclide of the type described above, are disposed within the body of the spherical container 41 and/or against the outside surface thereof to be rendered radioactive when a beam or beams of radiation, such as neutrons, are directed thereat and are absorbed by the particle or particles to effect such radioactivity which may comprise explosive and/or non-explosive radiation which may act to either force liquid or particulate drug material from the cells of the container 41, effect a chemical reaction resulting in such action or partially or completely destroy the container 41 to release its contents.

Disposed against and bonded to the outside surface 42 of the container 41 are shown a plurality of antibodies, such as monoclonal antibodies 45, which are targeted to a particular antigen, such as a disease or cancer cell or other cell located within the body of a living being to be treated, destroyed or otherwise affected by the action of chemical or biological agent carried by the container 41 and, if so constructed, by the radioactivity generated when the nuclide particle or particles are rendered radioactive as described.

Figure 6:
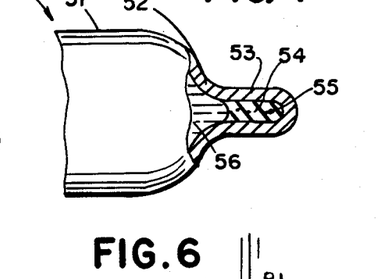
FIG. 6 is a side view in partial cross section of a portion of a container, such as a capsule, having a necked down portion containing one or more nuclide particles therein which may be rendered radioactive to render the necked down portion porous or to partially destroy same to permit the flow of contents from the container.

In FIG. 6 is shown a container assembly 50, which may be a preformed capsule or otherwise shaped implant having a container body 51 with a suitable sidewall 52 and having contents 56, such as one of the chemicals or biological agents described above, which contents are desired to be dispensed from a neck portion 53 of the container. Supported within the neck portion 53 is a solid material 54 containing one or more particles 55 of a nuclide of the type described. When such particle or particles 55 are rendered radioactive by externally applied radiation, they may heat and melt the material 54 or explode and rupture such material and a portion of the neck 53 of the container, thereby permitting the contents 56 to flow from such container, either by capillary action if the neck 53 is of a capillary construction, by internal pressure created by the heat of radiation or existing within the container, by gravity or osmosis effected when the wall 52 of the container and/or the filling material 54 is rendered porous or when porous filling material 54 is exposed to the exterior of the container when a portion of the wall of the neck 53 or the neck is ruptured or destroyed when a particle or particles 55 become radioactive.

Figure 7:
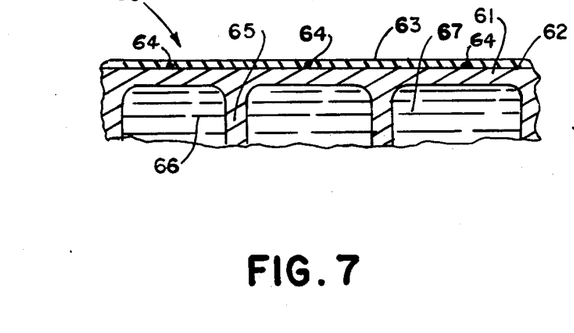
FIG. 7 is a side view in cross section of a portion of a container having multiple cells containing a drug or drugs and means for selectively effecting the dispensing of the contents of each cell.

In FIG. 7 is shown a portion of a container 60 having a sidewall 61 and a plurality of interior wall portions 65 extending completely through the container to provide a plurality of separate chambers 66 separated by such wall portions 65. Each of the chambers 66 may contain different portions of the same chemical or biological agent or different chemicals or biological agents.

Disposed against select portions of the sidewalls 61 and either bonded to the exterior surface 62 of the container 60 or supported within a material 63 coating such sidewall, are a plurality of particles 64 of a nuclide. In FIG. 7, one particle 64 is shown aligned with each of the chambers 66 of the container although a multiple of such particles may be so aligned and disposed.

When a beam or beams of radiation, such as neutrons, are selectively directed at selected portions of the sidewall 61 and the particle or particles 64 align therewith, the selected portions of the sidewall may be ruptured, rendered porous or have small openings formed therein when the particle or particles of nuclide are rendered active as described, thereby selectively affecting the dispensing of the contents 67 of the chamber or chambers 66 having their sidewall portions ruptured or rendered porous when the selected nuclide particle or particles become radioactive.

Figure 8:
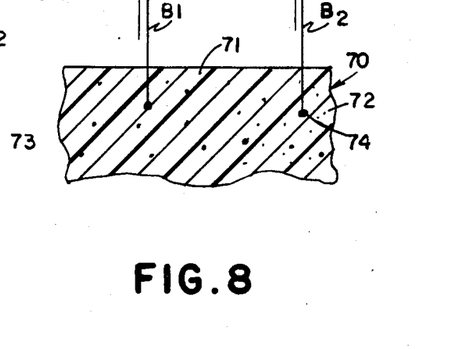
FIG. 8 is a side view in cross section of a portion of a drug unit containing one or more particles of a nuclide which may be rendered radioactive with suitable radiation and may effect the selective and partial destruction or dispensing of FIG. 9 is a side view of a composite drug unit formed of an assembly of an antibody and a killer cell, such as a lymphocyte or phage.

In FIG. 8 is shown another form of the invention comprising a material 7, which may form a drug unit or a multitude of such drug units, a filament or larger capsule which is injected or injested into a living being or applied by means of a catheter to a selected portion of the body or a body duct of such living being. The material 70 is formed of solid material 71 which may be solid through and through or formed with cells or pores containing a chemical or biological agent. The material 71 may also comprise a chemical or biological agent to be selectively dispensed at a select site within a living being for one or more of the purposes of destroying, modifying, or otherwise beneficially affecting tissue, cells or other material existing within a living being.

In addition to the provision of particles 72 of a chemical or biological agent within the material 71, a plurality or multitude of particles 74 of a nuclide are provided which, when selectively activated by the selected application of a radiation beam, such as beams B1 and B2 illustrated in FIG. 8, to generate radiation for effecting either the selected particalizing of portions of the material 71 and its contents by the resulting miniature nuclear explosions or when the heat of such nuclear reactions is generated and causes material to be dispensed from the cells of solid material 71 or to melt small quantities of such material and/or its contents. The particles 74 may also be bonded to select portions of the exterior surface of material 71 and, when rendered radioactive, as described, may cause select quantities of such material to be exploded or particalized and dispensed from the surface of the material into surrounding fluid or tissue for treating same as described above.

While antibodies have been described which target to select or specific antigens, such as defined by specific types of cancer cells, it is noted other forms of cells seeking or targeting biological material, such as antigen fragments and certain white blood cells, such as pahges, which are surface shaped to permit their targeting to specific antigens, may also be employed for such purposes as those described, to dispose one or more killer cells, chemical or biological agents for fighting disease, such as cancer, at the disease site. Accordingly, where employed herein, the term antibody shall imply any suitable material, cell or particle capable of targeting and attaching the drug unit to a specific type of cell antigen, such as existing in a malignant or non-malignant tumor which is desired to be destroyed or reduced in size.

Figures 9, 10:
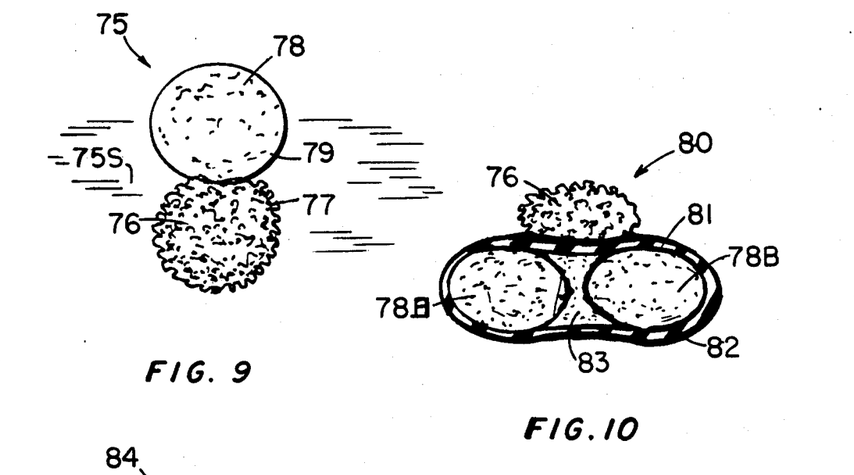

In FIG. 9 is shown yet another form of the invention comprising a drug unit 75, a multitude of which are formed as described and may be employed per se in a liquid medium 75S in the treament of a disease, such as cancer. The unit 75 is formed of an antibody, such as a monoclonal antibody which is cloned or bioengineered and produced outside the body of a person suffering from a specific type of cancer, wherein such antibody 76 is operable to target to cancer cells of the cancer existing in the patient to be treated. Such targeting or attachment to such a specific cancer cell type is effected by the particular configuration of the exterior surface 77 of the antibody 76. Bonded to a portion of the outer surface 77 of the antibody 76 is a single white blood cell or lymphocyte 78 which is designed to attack and weaken or destroy foreign bodies, such as cancer cells existing in living tissue, bone or blood. The lymphocyte or macrophage 78 is preferably produced from the patient's own white blood cells or lynphocytes, such as by extracting a quantity thereof from a sample of the patient's blood and growing or activating same with a biological stimulating agent, such as interleukin-2 to form so called lymphokine-activated killer cells which form the unit or portion 78 of the drug unit 75.

The antibody 76 may be produced by a number of known methods including some described including those described in U.S. Pat. No. 4,150,149 and those disclosed by Herberman, "Immunodiagnosis of Cancer", in Fleisher ed., "The Clinical Biochemistry of Cancer", page 347 (American Association of Clinical Chemists, 1979), in U.S. Pat. No. 4,460,561, in the references thereof and in other publications. Bonding or attachment of the antibody 76 to the killer cell 78 may be effected by means of a derivatizing agent as described in my copending patent application Ser. Nos. 614,021 and 614,038, both filed May 25, 1984 or by methods such as described in Goldenberg U.S. Pat. Nos. 4,460,561; 4,361,554; 4,348,376 or 4,444,744. The liquid medium 75S in which the drug unit 75 may be provided, stored and administered for treatment to a living being having cancer may be a neutral or active fluid such as water, various esters, acids or other agents as described in my copending applications or the prior art, such as set forth above.

A multitude of the drug units 75 may be employed per se in a dose or a plurality of doses injected into the tissue or blood of a patient at select times during treatment to permit the monoclonal antibody portion of each unit to target the unit to a cancer cell, such as existing in or on a cancerous tumor. The drug units 75 may also be employed mixed in a fluid medium with a multitude of killer cells 78 employed per se or encapsulated in a biodegradeable shell, microcapsule or coating to be released therefrom upon biodegradation in body fluid such as the blood.

Notation 79 refers to a coating of a biodegradable organic or synthetic polymer which, in a modified form of the invention, may surround the lymphocyte or killer cell 78, so as to retain same inactive for a time interval sufficient to permit the antibody portion 76 of the drug unit to target to a cancer cell and/or before the coating or microcapsule 79 biodegrades under the action of body fluid.

In a preferred form of the invention, both the monoclonal antibody 76 and the lymphocyte 78 are operable, upon targeting to a cancer cell or group of cancer cells to respectively attack such cell or cells and cooperate in destroying same in a process which progresses as additional drug units flow to the cancer or tumor site, target to respective cancer cells as they become exposed and dimish or destroy the entire tumor or malignancy.

In the embodiment of FIG. 9 employing a coating or capsule 79 completely surrounding the killer cell 78, the antibody 76 is attached to a portion of the outer surface of such coating 79.

FIG. 10 illustrates a modified form of drug unit 80 formed of two or more macrophages or lymphocytes, denoted 78A and 78B of the type described, which are encapsulated within a microcapsule, vesicule, liposome or coating denoted 81. Bonded or attached to the outer surface 82 of the coating or capsule 81 is an antibody, such as a monoclonal antibody targeted to a specific type of cancer antigen as described. Methods, as described in my copending application Ser. No. 614,038 or in the prior art presented above, may be employed to attach or bond the antibody 76 to the outer surface 82 of the coating or microcapsule 81. Notation 83 refers to a liquid medium also contained within the microcapsule 81 which may contain or comprise interlukin-2 extracted from the blood of the patient or produced by proper bio-engineering techniques outside of the body which may serve to maintain, grow and/or activate the lymphocytes 78A, 78B, etc. existing the the capsule or liposome 81 until they are released therefrom, after the capsule is ruptured, dissolved or biodegraded at a time after the drug unit 80 has become targeted to a cancer cell, thus releasing the killer cells immediately adjacent the cancer cell or tumor permitting them to cooperate per se or with the antibody 76 in killing or destroying cancer cells.

The fluid 83 contained in the microcapsule 82 may also comprise, in it entirety or in part, one or more other fluids which contain one or more radioactive isotopes, dyes or other detectable markers useful in generation of an image of the cancer site and/or in treating the cancer thereof. Such liquid may also contain a normally inactive nuclide, such as boron-10 or as described in the above mentioned copending patent applications, adapted to become activated by externally generated and applied radiation, such as a beam of neutrons, to effect release of the contents of the microcapsule at the cancer site, as described above. Notation 83 may also refer to a solvent or biodegrading chemical operable to biodegrade the wall of the capsule 81 after sufficient delay to permit the antibody 76 to target the drug unit to a cancer cell.

Figure 11:
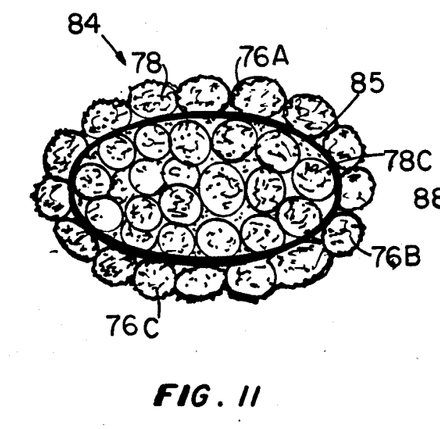
FIG. 11 is a side view of a modified form of the unit of FIG. 10.

In FIG. 11 is shown a modified form of a drug unit 84 composed of a plurality of lymphocytes or killer cells 78 bonded to the outside surface of a microballoon or microcapsule 85 containing a plurality of similar killer cells or lymphocytes 78C encapsulated therein, with or without a liquid as described above. One or more monoclonal antibodies, a number of which denoted 76A, 76B, 76C, 76D, etc. are bonded to the outside surface of capsule or liposome 85 for targeting the drug unit to one or more specific cancer cells.

Figure 12:
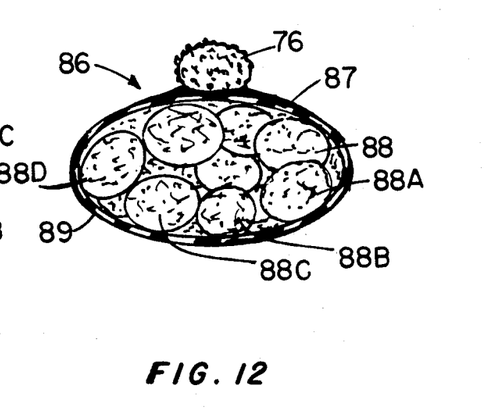
FIG. 12 is a side view of a modified form of the unit of FIG. 10.

In FIG. 12 is shown another form of the invention wherein one or more monoclonal antibodies attached to a microcapsule or vesicule such as a liposome containing a plurality of separate biological units encapsulated therein, target such microcapsule to a cancer or tumor in a living being wherein the contents thereof act over an extended period of time in reacting on or destroying cancer cells in the vicinity thereof. A drug unit 86 is formed of a microcapsule 87 which may be formed on a biodegradable organic or inorganic polymer, a protien or fat globule, such as a liposome, or a living cell containing a plurality of smaller units 88, which are denoted 88A, 88B, 88C, etc., encapsulated therein. The capsule 87 is either operable to dissolve or biodegrade in the presence of body fluid and/or to be rendered porous by chemical or biological action or to be penetrated and opened by radioactivity, as described, so as to either slowly release its contents or suddenly release same. Each of the smaller units 88 may comprise one or more macrophages or lymphocyte killer cells, as described, employed per se or covered with a thin film or shell of biodegradeable organic or inorganic polymer, which coatings operate to biodegrade at different times in body fluid to expose or release the contents thereof, (one or more killer white blood cells), to the targeted cancer location to progressively destroy cancer cells. Targeting to a cancer site may be effected by one or more monoclonal antibodies 76 bonded to the surface of the capsule 87. The capsule 86 or a plurality thereof, may also be inserted by surgery, a catheter or hypodermic needle into or adjacent a tumor to release its contents, as described, over an extended period of time so as to progressively destroy a tumor as well as free travelling cancer cells. Notation 89 refers to a bioadhesive coating all or a select portion of the outer surface of the capsule 87 for binding such capsule to tissue such as cancer tissue or tissue adjacent same. Assembly and bonding of such antibody or antibodies to the outer surface 87S of the capsule 87, which may comprise a lipid vesicule or liposome, a red blood cell, or a biodegradable organic or inorganic polymer microballoon, may be effected by means of a derivatizing agent or other means as described in my copending patent applications.

Additional features and modification to the described drug compositions and methods for producing and applying same are noted as follows:

1. For the treatment of cancer, antibodies, such as monoclonal antibodies which are marker specific, may be produced by conventional methods known in the art wherein such antibodies or antibody fragments are targeted to a specific carcinoembryonic antigen (CEA) and are bound to any of the described killer cells, biodegradeable or dissolvable coatings thereon or microcapsules containing one or more of such lymphocytes, macrophages or the like or time release containers for same.

2. Various biodegradeable or body fluid dissolvable organic and inorganic polymers may be employed for the described lymphocyte or killer cell coating and encapsulating materials, such as described in U.S. Pat. No. 4,434,153 which discloses which discloses various waxes, cellulosic materials polyvivnyl polymers and the like which will dissolve or biologically degrade to destroy encapsulation and release their contents at times which may vary from minutes after initial injection or exposure to hours thereafter depending on the coating or encapsulation material and its thickness. Polymers for forming such coatings and microcapsules are described in such U.S. Pat. Nos. 3,811,444; 3,867,519; 3,888,975; 3,971,367; 3,993,057 and 4,138,344.

3. In a preferred form of the embodiments defining drug units, such as those illustrated in FIGS. 1,3,4,5,9 and 10, the average maximum dimension or diameter of the drug units is preferably in the range of four to ten microns which will permit the drug unit to flow through capillaries. Larger diameter drug units may be produced to flow through blood vessels or to be disposed directly in tumors by needle or surgery.

4. The drug units illustrated in FIGS. 10, 11 and 12 may contain a number of biological units of the same or different types including antibodies, activated lymphocytes, anbiotic and anti-viral agents as well as one or more chemicals for cooperating in the treatment and destruction of a cancer or tumor to which the drug units target.

5. The drug unit embodiments illustrated in FIGS. 3, 4, 7, 10, 11 and 12 may be fabricated with a chemical contained within the microcapsules thereof, which chemical serves to react on the wall of the microcapsule or vesicule of the unit and to dissolve, biodegrade or render such was porous a time delay after formation of the drug unit sufficient to permit it to be administered to a patient and permit the drug unit to become targeted to a specific disease site, such as a tumor or malignancy.

6. In the embodiments illustrated in FIGS. 4, 5, 9, 10, 11 and 12, the drug units may be constructed such that, when targeting of the antibody portion takes place, physical separation of the killer cell from the antibody takes place of the microcapsule containing one or more of such killer cells is ruptured or weakened permitting it to be opened thereafter by internal pressure, biodegradation or physical and/or chemical activity associated with the contents thereof. If the antibody itself is operable to attack the cell of the antigen to which it is attached, its activity in attacking such cell may be such as to cause it to detatch itself from the surface of the killer cell or the microcapsule therefor and, in so doing, to provide an opening across the portion thereof to which it was attached to permit the contents of such microcapsule to be released at the site of the antigen to permit the lymphocyte(s) to attack one or more cells in the vicinity of their release.

7. In any of the embodiments illustrated in the drawings, a biodegradeable bioadhesive may be applied to the surface of the microcapsule, the biodegradeable coating on the killer cell or activated lymphocyte or a plurality of same bonded to a capsule or liposome for bonding same to tissue at the site to which they are disposed or targeted. Such bioadhesive may also be contained within one or more biodegradeable microcapsules to be released therefrom upon biodegradation or dissolution of their container(s) at the targeted site so as to bond the drug units or the killer cell portions thereof to tissue at the site until such microcapsules containing the killer cells biodegrade to release same therefrom.

8. The drawings provided herewith are not necessarily drawn to scale nor are the relative sizes of the components necessarily shown to the same scale.

9. In the embodiments of the invention illustrated in FIGS. 1, 3, 4, 9, 10, 11 and 12, the microcontainers or microcapsules employed to encapsulate the one or more phages, lymphocytes or similar chemical and/or biological unit or units useful in destroying or weakening cancer cells to which they are targeted or disposed next to, may be made of cells from living tissue or blood, such as red blood cells and/or other cells which have been biologically engineered as a result of gene splicing and the like and grown by incubation or other means outside of the body.

10. In the embodiments illustrated in FIGS. 9-12, the antibody or antibody fragments 76 may be bound to the microcapsule and the latter may be so constructed that, when the antibody targets or attaches itself to an antigen, such as an antigen of or associated with a cancer cell or cells, its weakens the microcapsule wall, creates an opening therein or ruptures same permitting the contecnts thereof to be freed from encapsulation and the killer cells and/or other biological or cemical elements contained therein to be dispensed adjacent to or against the cancer cell or cells for weakening or destroying same.

11. The techniques previously described, such as illustrated in FIGS. 1 and 2, for penetrating, weakening, boring a hole in or rupturing the coating, liposome or microcapsule surrounding the killer cell or cells at the site of the cancer.

12. The methods described in U.S. Pat. Nos. 4,310,506 and 4,448,765 may be employed int the production of microcapsules such as liposomes containing killer cells and the likes as illsutrated in FIGS. 1, 3, 4, 9, 10, 11 and 12.

What is claimed is:

1. drug composition for use in the treatment of a disease, such as cancer, defined by a multitude of drug units composed of:
   (a) a first drug unit component which is targeted to a specific antigen of a disease existing within a living being,
   (b) a second drug unit component containing at least one cell destroying killer cell,
   (c) said first drug unit component and said second drug unit component defining a unitary assembly wherein a portion of the surface of said first component extends outwardly from said assembly and is free to engage and become attached to antigens existing within a living being to which said drug unit is administered.

2. A drug composition in accordance with claim 1 wherein said first drug unit component comprises an antibody such as a monoclonal antibody targeted to a specific type of cancer cell.

3. A drug composition in accordance with claim 1 wherein sid first drug unit component comprises an antibody fragment targeted to carcinoembronic antigen (CEA) and the drug composition formed of a multitude of such units is in a fluid injectable form.

4. A drug composition in accordance with claim 1 provided in an injectable fluid form and further including a multitude of cell destroying killer cells mixed with said multitude of drug units in said fluid.

5. A drug composition in accordance with claim 1 wherein said second drug unit component is a lymphocyte which has been incubated with interlukin-2 and defines a lymphokineactivated killer cell deadly to a specific cancer, said lymphocyte being derived from the blood of a person to whom such drug composition is administered.

6. A drug composition in accordance with claim 1 including a material interposed between and bonded to said first and said second drug unit components preventing interaction between the two components.

7. A drug composition in accordance with claim 6 wherein said material which is interposed between said first and second drug unit components comprises a coating completely surrounding said second drug unit component, the material comprising said coating being degradeable to expose said second drug unit component within the body of a living being receiving said drug composition at a rate such that exposure of said second drug unit component occurs after targeting of the drug unit to a specific type of antigen within the body occurs.

8. A drug composition in accordance with claim 1 including a microcapsule surrounding and encapsulating said second drug unit component and means for releasing said second drug component from said microcapsule after the drug unit has become targeted to an antigen, such as defining a cancer cell existing in a living being to whom such drug composition has been administered.

9. A drug composition in accordance with claim 8 wherein said first drug unit component is composed of a pluralty of monoclonal antibodies or fragments of monoclonal antibodies targeted to at least two different types of antigens defining different types of cancer cells, and a plurality of said cell destroying killer cells contained within said microcapsule.

10. A drug composition in accordance with claim 6 wherein said material interposed between said drug unit components comprises a microcapsule, a plurality of said second drug unit components encapsulated within said microcapsule, said microcapsule being biodegradeable after said drug composition is administered to a living being in a manner to release the killer cells therefrom after said drug unit has been targeted to the antigen defined by said first drug unit component.

11. A drug composition in accordance with claim 1 including a plurality of said drug unit components and respective biodegradeable encapsulation means for respective of said second drug unit components, means for cuasing respective quantities of said respective encapsulation means to biodegrade at different times after a dose of said drug composition has been administered to the body of a patient being treated therewith and wherein at least certain of said drug unit components are so released after the drug unit becomes targeted to an antigen of a cancer cell existing within the body of said patient.

12. A drug composition in accordance with claim 1 including a lipid vesicule, surrounding and encapsulating said drug unit component, said first drug unit component being bound to the outside surface of said vesicule.

13. A drug composition in accordance with claim 1 including means for encapsulating said second drug unit component and means for releasing said cell destroying killer cell from such encapsulation, and a biodegradeable bioadhesive coating said encapsulation means for binding said drug unit to the surface of tissue in the vicinity of the antigen to which said first drug unit component targets to.

14. A drug composition for use in treating a tumor, such as a malignancy, formed of a multitude of drug units, which drug units comprise:
    (a) a killer cell in the form of a lymphocyte rendered deadly to cells of a malignancy when in contact
    (b) encapsulating means in the form of a wall of material surrounding said killer cell,
    (c) an antibody having a surface portion configured to attach said antibody to a cell of said malignancy,
    (d) said antibody being bound to the outside surface of said wall surrounding said killer cell wherein a sufficient portion of the surface of said antibody protrudes from said wall to permit said antibody to target and become attached to a cell of said tumor, and
    (e) means for releasing said killer cell from encapsulation by said encapsulating means to permit it to attack a cell of a malignancy adjacent said drug unit after said antibody has become targeted to said malignancy.

15. A drug composition in accordance with claim 14 said wall of said material surrounding and encapsulating said killer cell normally separates said antibody from said killer cell and prevents said killer cell from attacking normal body cells while said drug unit is passing through the body to the site of a malignancy.

16. A drug composition in accordance with claim 14 including means for providing an opening in the wall of said encapsulating material after the drug unit targets to targets to an antigen within the body of a living being to which said drug composition has been administered.

17. A method of treating a tumor, such as malignancy, existing in a living being comprising:
    (a) forming a drug composition of a multitude of drug units, which drug units are composed of a biological element targeted to an intracellular marker substance, produced by or associated with a tumor to be treated, and at least one killer cell, such as a phage contained by said drug unit and carried thereby,
    (b) administering a dose of said drug composition to a living being having a tumor to which said antibody is targetable and permitting drug units of said dose to target to respective portions of said tumor by permitting the antibodies thereof to attach to respective cells of said tumor,
    (c) after said drug units become targeted adjacent the tumor, releasing the killer cells thereof from the drug units and permitting said killer cells to attack respective cells of the tumor and to destroy the cells they attack,
    (d) providing a sufficient number of said drug units administered to the body of said living being to effect the destruction of said tumor under the action of killer cells.

18. A method in accordance with claim 17 wherein step (c) is effected by encapsulating said killer cells in respective microcontainers and releasing said killer cells from said microcontainers adjacent said tumors.

19. A method in accordance with claim 18 wherein said killer cells are released from said microcontainers by destruction of the microcontainers at the sites of said tumor.

20. A method in accordance with claim 17 wherein said drug units are formed with a plurality of killer cells disposed in a microencapsulating means from which encapsulating means said plurality of killer cells are time control released in a manner to permit individual killer cells to attack different cells of said tumor.

* * * * *